March 12, 1963 E. S. BOERNER Plant Pat. 2,238
ROSE PLANT
Filed May 28, 1962
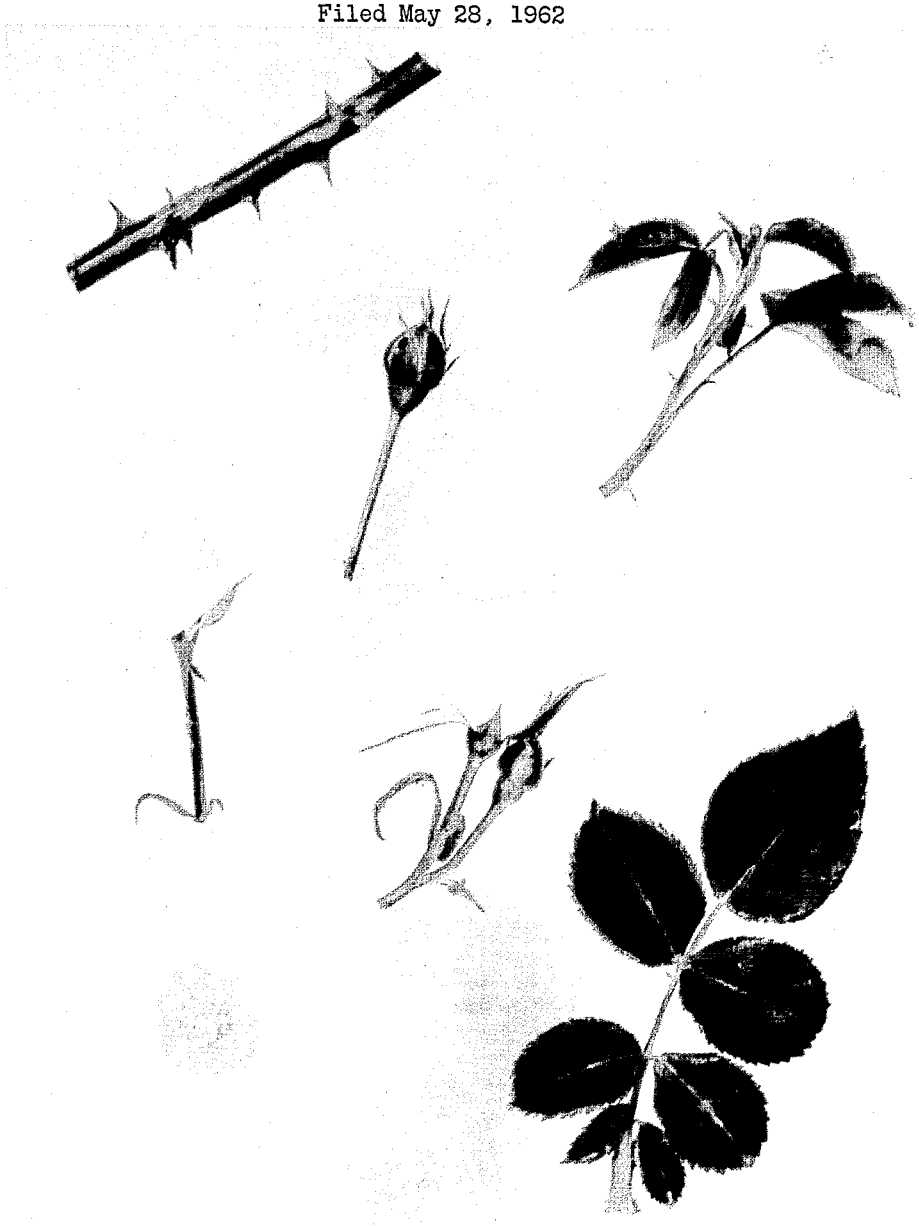
Inventor.
E. S. Boerner
By: Robb & Robb
Attorneys.

United States Patent Office

Plant Pat. 2,238
Patented Mar. 12, 1963

2,238
ROSE PLANT

Eugene S. Boerner, Newark, N.Y., assignor to Jackson & Perkins Company, Newark, N.Y., a corporation of New York Filed May 28, 1962, Ser. No. 198,384
1 Claim. (Cl. 47—61)

The present invention relates to a new and distinct variety of rose plant of the floribunda class, which was originated by me by crossing an unnamed and unpatented seedling of "Pinocchio" (Plant Patent No. 484) with the variety "Spartan" (Plant Patent No. 1,357).

The primary objective of this breeding was to improve the "Spartan" floribunda variety by developing therein a more floriferous flowering habit, combined with unfading flower color. This objective was fully achieved, along with other desirable improvements, as evidenced by the following unique combination of characteristics which are outstanding in the new variety and which distinguish it from its parents, as well as from all other varieties of which I am aware:

(1) An upright and bushy habit of plant growth;

(2) An extremely floriferous flowering habit, with the flowers forming large mounds; and (3) A distinctive and unfading general color tonality of the flowers corresponding to Thulite Pink, lightly overcast with La France Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Pinocchio."

*Pollen parent.*—"Spartan."

Classification:

*Botanic.*—Floribunda.

*Commercial.*—Floribunda.

*Flower*

(Observations made from specimens grown outdoors at Newark, New York during the latter part of the month of August.)

Blooming habit: Recurrent—continuous.

Bud:

*Size.*—Medium.

*Form.*—Ovoid; is not affected by wet or hot weather.

*Color.*—When sepals first divide—Nopal Red, Plate 1. When petals begin to unfurl—Cameo Pink, Plate 26, with center lightly overcast with Cartridge Buff, Plate 30, and with the outer edges lightly overcast with Thulite Pink, Plate 26. When half-blown: inside of petals—Eosine Pink, Plate 1, overcast with Begonia Rose, Plate 1; reverse of petals—Ivory Yellow, Plate 30, with outer edges overcast with Thulite Pink, Plate 26.

*Sepals.*—Slightly serrated and branched; curl back when petals begin to unfurl. Color: inside—Sea-Foam Green, Plate 31; outside—Light Bice Green, Plate 17

*Calyx.*—Color—Light Bice Green, Plate 17. Shape—pear. Size—small. Aspect—smooth. Odor when rubbed—none.

*Peduncle.* — Length — medium. Aspect — smooth. Strength — erect; slender. Color — Light Elm Green, Plate 17.

*Opening.*—Opens up well; is not affected by adverse weather conditions.

Bloom:

*Size.*—Medium. Average size when fully expanded—4 inches.

*Borne.*—Both several together and in clusters forming rounded mounds of flowers; very floriferous.

*Stems.*—Medium length; strong.

*Form (when first open).*—Cupped. Permanence—retains its form to the end, but outer petals curl back.

*Petalage.*—Double (full but open center). Number of petals under normal conditions—from 30 to 35.

*Color.*—Center of flower—La France Pink, Plate 1, lightly overcast with Thulite Pink, Plate 26. Outer petals—Flesh Pink, Plate 13, lightly overcast with La France Pink, Plate 1. Base of petals (aiglet)—Picric Yellow, Plate 4. Inside of petals—Thulite Pink, Plate 26, lightly overcast with La France Pink, Plate 1. Reverse of petals—La France Pink, Plate 1, very lightly overcast with Rose Pink, Plate 12. General tonality from a distance—La France Pink, Plate 1, lightly overcast with Thulite Pink, Plate 26.

*Discoloration.*—General tonality at end of first day—La France Pink, Plate 1, overcast with Thulite Pink, Plate 26. Second day—La France Pink, Plate 1, lightly overcast with Thulite Pink, Plate 26. Third day—La France Pink, Plate 1, lightly overcast with Thulite Pink, Plate 26.

Petals:

*Texture.*—Leathery; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.* — On the plant — long. As cut flower—long.

*Genital Organs*

Stamens, anthers: Small; many; regularly arranged around styles. Color—Orange, Plate 3.

Stamens, filaments (threads): Medium length. Color—Pale Lemon Yellow, Plate 4.

Pollen: Color—Capucine-Buff, Plate 3.

Styles: Bunched; uneven length; medium length; thin.

Stigmas: Color—Pale Orange-Yellow, Plate 3.

Ovaries: All enclosed in calyx.

Hips: None.

Seeds: None.

*Plant*

Form: Bush.

Growth: Vigorous; upright; bushy.

Foliage: Compound of 5–7 leaflets.

*Size.*—Large.

*Quantity.*—Abundant.

*Color.*—New foliage: upper side—Oxblood Red, Plate 1; under side—Garnet Brown, Plate 1, with center rib Light Yellowish Olive, Plate 30. Old foliage: upper side—Varley's Green, Plate 31; under side—Light Bice Green, Plate 17.

*Shape.*—Oval.

*Texture.* — Upper side — leathery. Under side—smooth.

*Ribs and veins.*—Ordinary.
*Edge.*—*Serrated* (saw-toothed).
*Serration.*—Both double and single; small.
*Leaf stem.*—Color—Mignonette Green, Plate 31. Under side—prickly.
*Stipules.*—Long; bearded.

Wood:
*New wood.*—Color—Malachite Green, Plate 32. Bark—smooth.
*Old wood.*—Color—Light Cress Green, Plate 31. Bark—smooth.

Thorns:
*Thorns.*—Quantity; on main stalks from base—ordinary; on laterals from stalk — ordinary. Form — narrow base; medium length; hooked downward. Color (when young)—Old Rose, Plate 13. Position—irregular.

*Prickles.*—Quantity; on main stalks—none; on laterals—none.
*Short needles.*—Quantity; on main stalks—none; on laterals—none.

I claim:

A new and distinct variety of rose plant of the floribunda class, substantially as herein shown and described, characterized particularly as to novelty by the unique combination of an upright and bushy habit of plant growth, an extremely floriferous flowering habit, with the flowers forming large mounds, and a distinctive and unfading general color tonality of the flowers corresponding to Thulite Pink, lightly overcast with La France Pink.

No references cited.